US010016527B2

(12) United States Patent
Long (10) Patent No.: US 10,016,527 B2
(45) Date of Patent: Jul. 10, 2018

(54) MATERIALS AND METHODS FOR REPAIR OF CARTILAGE DEFECTS (71) Applicant: Orthovita, Inc., Malvern, PA (US)

(72) Inventor: Marc Long, Denville, NJ (US)

(73) Assignee: Orthovita, Inc., Malvern, PA (US)

( * ) Notice: Subject to any disclaimer, the term of this patent is extended or adjusted under 35 U.S.C. 154(b) by 446 days.

(21) Appl. No.: 13/793,142

(22) Filed: Mar. 11, 2013

(65) Prior Publication Data
US 2014/0114280 A1    Apr. 24, 2014

Related U.S. Application Data (60) Provisional application No. 61/717,254, filed on Oct. 23, 2012.

(51) Int. Cl.
A61B 17/20 (2006.01)
A61L 27/24 (2006.01)
A61B 17/16 (2006.01)

(52) U.S. Cl.
CPC .............. *A61L 27/24* (2013.01); *A61B 17/16* (2013.01); *A61B 17/1604* (2013.01); *A61B 17/1631* (2013.01); *A61L 2430/06* (2013.01)

(58) Field of Classification Search
CPC .. A61L 26/0052; A61L 26/0066; A61L 27/24; A61L 24/30106; A61L 26/00; A61L 2430/06; A61B 17/16; A61B 17/1604; A61B 17/1631
USPC ........ 424/491; 604/22, 506; 606/80, 53, 606
See application file for complete search history.

(56) References Cited

U.S. PATENT DOCUMENTS

| 4,649,909 A | 3/1987 | Thompson |
| 4,743,499 A | 5/1988 | Volke |
| 5,024,841 A | 6/1991 | Chu et al. |
| 5,110,604 A | 5/1992 | Chu et al. |
| 5,219,328 A | 6/1993 | Morse et al. |
| 5,290,552 A | 3/1994 | Sierra et al. |
| 5,318,524 A | 6/1994 | Morse et al. |
| 5,407,671 A | 4/1995 | Heimburger et al. |
| 5,616,689 A | 4/1997 | Shenoy et al. |
| 5,752,974 A | 5/1998 | Rhee et al. |
| 5,759,190 A | 6/1998 | Vibe-Hansen et al. |
| 5,763,411 A | 6/1998 | Edwardson et al. |
| 5,997,811 A | 12/1999 | Esposito |

(Continued)

OTHER PUBLICATIONS

Bedi et al., "Current Concepts Review Management of Articular Cartilage Defects of the Knee", The Journal of Bone & Joint Surgery, vol. 92:994-1009, 2010.

(Continued)

*Primary Examiner* — Kevin C Sirmons
*Assistant Examiner* — Tiffany Legette-Thompson
(74) *Attorney, Agent, or Firm* — Lerner, David, Littenberg, Krumholz & Mentlik, LLP (57) ABSTRACT In one embodiment, the present invention includes a method for repairing a cartilage defect including: preparing a cartilage defect by removing unwanted or damaged tissue; creating at least one perforation into or through subchondral bone, below and/or adjacent to the cartilage defect to induce the flow of bone fluid; allowing the bone fluid to bleed through the at least one perforation up into the cartilage defect to fill at least a portion of the cartilage defect; and applying a biomaterial into the defect to produce a clot for cartilage regeneration.

20 Claims, 7 Drawing Sheets

(56) References Cited

U.S. PATENT DOCUMENTS

| | | | |
|---|---|---|---|
| 6,096,309 | A | 8/2000 | Prior et al. |
| 6,110,484 | A | 8/2000 | Sierra |
| 6,277,394 | B1 | 8/2001 | Sierra |
| 6,283,980 | B1 | 9/2001 | Vibe-Hansen et al. |
| 6,310,267 | B1 | 10/2001 | Rapp |
| 6,352,558 | B1 | 3/2002 | Spector |
| 6,569,172 | B2 | 5/2003 | Asculai et al. |
| 6,762,336 | B1 | 7/2004 | MacPhee et al. |
| 6,866,668 | B2 | 3/2005 | Giannetti et al. |
| 6,967,261 | B1 | 11/2005 | Soerens et al. |
| 7,041,868 | B2 | 5/2006 | Greene et al. |
| 7,112,183 | B2 | 9/2006 | Binder et al. |
| 7,137,989 | B2 | 11/2006 | Asculai et al. |
| 7,141,072 | B2 | 11/2006 | Geistlich et al. |
| 7,148,209 | B2 | 12/2006 | Hoemann et al. |
| 7,317,134 | B2 | 1/2008 | Faasse, Jr. |
| 7,329,792 | B2 | 2/2008 | Buckman et al. |
| 7,427,293 | B2 | 9/2008 | Nycz et al. |
| 7,553,923 | B2 | 6/2009 | Williams et al. |
| 7,604,819 | B2 | 10/2009 | Huey et al. |
| 7,612,248 | B2 | 11/2009 | Burton et al. |
| 7,619,130 | B2 | 11/2009 | Nielsen et al. |
| 7,626,071 | B2 | 12/2009 | Masini |
| 7,700,819 | B2 | 4/2010 | Ambrosio et al. |
| 7,763,769 | B2 | 7/2010 | Johnson et al. |
| 7,879,105 | B2 | 2/2011 | Schmieding et al. |
| 7,902,420 | B2 | 3/2011 | Kase |
| 7,923,031 | B2 | 4/2011 | Moller |
| 7,923,431 | B2 | 4/2011 | Wolff |
| 7,968,114 | B2 | 6/2011 | Huey et al. |
| 8,084,664 | B2 | 12/2011 | Johnson et al. |
| 8,100,847 | B2 | 1/2012 | Fournet, II |
| 8,114,433 | B2 | 2/2012 | Huey et al. |
| 8,137,294 | B2 | 3/2012 | Baschnagel |
| 8,163,974 | B2 | 4/2012 | Ambrosio et al. |
| 8,251,998 | B2 | 8/2012 | Hoeppner et al. |
| 8,252,318 | B2 | 8/2012 | Huey et al. |
| 8,252,970 | B2 | 8/2012 | Buckman et al. |
| 8,257,731 | B2 | 9/2012 | Horn et al. |
| 8,257,732 | B2 | 9/2012 | Huey et al. |
| 8,343,537 | B2 | 1/2013 | Huey et al. |
| 2001/0014475 | A1 | 8/2001 | Frondoza et al. |
| 2002/0082692 | A1 | 6/2002 | van Blitterswijk et al. |
| 2002/0111576 | A1 | 8/2002 | Greene et al. |
| 2002/0173806 | A1 | 11/2002 | Giannetti et al. |
| 2004/0015115 | A1 | 1/2004 | Sinyagin |
| 2005/0222687 | A1* | 10/2005 | Vunjak-Novakovic ........ A61F 2/30756 623/23.63 |
| 2006/0058721 | A1 | 3/2006 | Lebner et al. |
| 2006/0079823 | A1* | 4/2006 | Utterberg ............... A61F 13/02 602/53 |
| 2006/0116620 | A1 | 6/2006 | Oyaski |
| 2006/0122548 | A1 | 6/2006 | Abrams |
| 2006/0129080 | A1 | 6/2006 | Bjornberg et al. |
| 2006/0142685 | A1 | 6/2006 | Addison et al. |
| 2006/0189910 | A1 | 8/2006 | Johnson et al. |
| 2007/0178132 | A1 | 8/2007 | Giannetti et al. |
| 2007/0203442 | A1 | 8/2007 | Bechert et al. |
| 2007/0276308 | A1 | 11/2007 | Huey et al. |
| 2007/0293801 | A1 | 12/2007 | May |
| 2008/0058692 | A1 | 3/2008 | Propp et al. |
| 2008/0064997 | A1 | 3/2008 | Flick |
| 2008/0081367 | A1* | 4/2008 | Sowemimo-Coker . A61K 35/15 435/325 |
| 2008/0097270 | A1 | 4/2008 | Utterberg et al. |
| 2008/0108923 | A1 | 5/2008 | Sinyagin |
| 2008/0108927 | A1 | 5/2008 | Sinyagin |
| 2008/0132821 | A1 | 6/2008 | Propp et al. |
| 2008/0177214 | A1 | 7/2008 | Robertsson et al. |
| 2008/0183119 | A1 | 7/2008 | Joshi |
| 2008/0269674 | A1* | 10/2008 | Stone ................ A61B 17/1635 604/80 |
| 2009/0030361 | A1 | 1/2009 | Bach |
| 2009/0076430 | A1 | 3/2009 | Simpson et al. |
| 2009/0157081 | A1* | 6/2009 | Homan ............... A61B 17/1764 606/80 |
| 2009/0177135 | A1 | 7/2009 | Rogers et al. |
| 2009/0187130 | A1 | 7/2009 | Asmus et al. |
| 2009/0299371 | A1* | 12/2009 | Steiner ............... A61B 17/1675 606/79 |
| 2009/0306676 | A1* | 12/2009 | Lang et al. ................. 606/102 |
| 2010/0008973 | A1* | 1/2010 | Galili ............... A61K 47/48815 424/443 |
| 2010/0015102 | A1* | 1/2010 | Iwasaki ................ A61L 27/20 424/93.7 |
| 2010/0111846 | A1* | 5/2010 | Boyden ............... A61K 9/0019 424/1.29 |
| 2010/0152615 | A1* | 6/2010 | Mark ................ A61B 10/0275 600/567 |
| 2010/0178355 | A1 | 7/2010 | Hoemann et al. |
| 2010/0318052 | A1 | 12/2010 | Ha et al. |
| 2011/0021964 | A1* | 1/2011 | Larsen ............... A61L 26/0066 602/47 |
| 2011/0060296 | A1 | 3/2011 | Threlkeld et al. |
| 2011/0243913 | A1* | 10/2011 | Antonio ............... A61K 33/42 424/94.5 |
| 2012/0046586 | A1 | 2/2012 | Gurtner et al. |
| 2012/0203231 | A1 | 8/2012 | Long et al. |

OTHER PUBLICATIONS

Chen et al., European Cells and Materials, vol. 16, Supp. 4, p. 7, 2008.

Chen et al., Journal of Orthopaedic Research, pp. 1432-1438, Nov. 2009.

Chen et al., Poster No. 538, 54th Annual Meeting of the Orthopaedic Research Society, San Francisco, CA Mar. 2008.

Cole et al., American Journal of Sports Medicine, vol. XX, No. X, 2011.

Falah et al., "Treatment of articular lesions of the knee", International Orthopaedics (SICOT) (2010) 34:621-630.

Fortier et al., "Science and Animal Models of Marrow Stimulation for Cartilage Repair", Journal of Knee Surgery, vol. 25, pp. 3-8, 2012.

Hoemann et al., "Chitosan-glycerol phosphate/blood implants improve hyaline cartilage repair in ovine microfracture defects", JBJS, 87-A (12): 2671-2686 (2005).

Insall et al., The Journal of Bone and Joint Surgery, vol. 49B, No. 2, pp. 211-228, May 1967.

Marchand et al., "Solidification mechanisms of chitosan-glycerol phosphate/blood implant for articular cartilage repair", Osteoarthritis and Cartilage, 17: 953-960 (2009).

Mithoefer et al., "Chondral resurfacing of articular cartilage defects in the knee with the microfracture technique. Suregical Technique", The Jornal of Bone & Joint Surgery vol. 88-A, pp. 294-304, 2006.

Orthopaedic Specialsts Bryn Mawr Sports Medicine, "Patient Guide to Articular Cartilage Injuries", <www.orthspec.com>,(Date unkown).

* cited by examiner

MATERIALS AND METHODS FOR REPAIR OF CARTILAGE DEFECTS

CROSS-REFERENCE TO RELATED APPLICATIONS

The present application claims the benefit of the filing date of U.S. Provisional Patent Application No. 61/717,254 filed Oct. 23, 2012, the disclosure of which is hereby incorporated herein by reference.

BACKGROUND OF THE INVENTION

Cartilage is an avascular connective tissue made up of collagen and/or elastin fibers, and chondrocytes, all of which are embedded in a matrix. There are three main types of cartilage: elastic, fibrocartilage, and hyaline. Elastic cartilage is found in the outer ear and the epiglottis. Fibrocartilage is found between the bones of the spinal column, hips and pelvis. Hyaline cartilage can be found on the ends of bones which form joints, on the ends of the ribs, on the end of the nose, on the stiff rings around the windpipe, and supporting the larynx. Articular cartilage is a specialized type of hyaline cartilage which covers the surface of joints and provides a durable low friction surface that distributes mechanical forces and protects the joint's underlying bone.

Different types of collagen can be found in varying amounts in the collagen matrix, depending on the type of tissue. For example, hyaline cartilage, which is found predominantly in articulating joints, is composed mostly of type II collagen with small amounts of types V, VI, IX, X, and XI collagen also present. On the other hand, fibrocartilage, which can also be found in joints, is primarily composed of type I collagen. Additionally, the fibrocartilaginous tissue that sometimes replaces damaged articular cartilage is composed of type I collagen.

Loss of or damage to cartilage can lead to painful conditions such as osteoarthritis. Damage to cartilage can be caused by traumatic injury, disease and/or age. Since cartilage lacks nerves and blood vessels, it has very limited regenerative capabilities compared to other tissues. Consequently, the healing of damaged joint cartilage results in a fibrocartilaginous repair tissue that lacks the structure and biomechanical properties of normal cartilage. Over time, the repair tissue degrades and leaves damaged joint cartilage, which causes osteoarthritis and reduced movement in the joint.

A number of procedures are used to treat damaged cartilage. One common procedure includes lavage, arthroscopic debridement and repair through bone marrow stimulation. Bone marrow stimulation is generally conducted by microdrilling, abrasion or microfracture to penetrate into or through subchondral bone to induce bleeding and clot formation at the cartilage defect site. This promotes initial repair. However, the resulting formed tissue is often fibrous in nature and lacks the durability of normal cartilage. Furthermore, extensive bleeding at the defect site may also be detrimental to the joint tissues, potentially causing inflammation and degradation. Alternatively, minimal bleeding may occur such that the clot forms within the subchondral bone, resulting in insufficient migration of blood, bone marrow, cells, and the like, from the subchondral bone into the cartilage defect.

There is a need for a method for enhancing clot formation in a tissue repair site or defect site to, for example, overcome poor clot quality and prevent fibrous tissue formation over time. There is also a need for a method which limits bleeding into the joint for alleviating joint disease, pain and discomfort.

BRIEF SUMMARY OF THE INVENTION

Generally, the present invention includes methods and materials for use in repairing a defect in cartilage. The materials include, for example, instrumentation to perform bone marrow stimulation and a biomaterial suitable to form a clot at the cartilage defect site and to promote cartilage regeneration. Various methods are also described herein which utilize these materials to repair a cartilage defect, such as by creating a healing matrix for a cartilage defect in-situ.

In one embodiment, the present invention includes a method of enhancing clot formation in a tissue repair site or defect site. The tissue may be cartilage, and more specifically articular cartilage, or alternatively any other tissue in the human body. In one aspect, the method includes enhancing clot formation and healing in a tissue repair site or defect site via the use of a biomaterial such as a surgical hemostat or the like. The method may also include creating at least one perforation into or through the subchondral bone, adjacent to and/or below the tissue defect site (in this instance, a cartilage defect site), to induce the flow of bone fluid, or induce bleeding, up into the cartilage defect to fill at least a portion of the defect; and applying a biomaterial or surgical hemostat to the defect such that the biomaterial, together with the bone fluid, may combine to completely fill, or at least substantially completely fill, the cartilage defect in order to achieve an enhanced clot within the cartilage defect and cartilage regeneration. Unlike other methods, the present invention method does not require the use of implants or substrates to fill the perforations in the subchondral bone. In certain embodiments, the perforations are left unfilled though incidental intrusion of the biomaterial into the subchondral bone may occur. The clot formation may occur in-situ, through the interaction of the applied biomaterial and the bone fluid.

In another embodiment, the present invention includes a method of repairing a cartilage defect, the method including forming an enhanced clot in the cartilage defect through the application of a surgical hemostat. The method may also include the step of creating at least one perforation into or through subchondral bone below and/or adjacent to the cartilage defect, to thereby allow bone fluid to bleed through the at least one perforation up into the cartilage defect to fill at least a portion of the cartilage defect. The enhanced clot may be produced through the interaction of the surgical hemostat and the bone fluid within the cartilage defect, such that the clot may assist in cartilage regeneration within the defect.

In yet another embodiment, the present invention includes a method for repairing a cartilage defect including: preparing a cartilage defect by removing unwanted or damaged tissue; creating at least one perforation into or through subchondral bone, below and/or adjacent to the cartilage defect to induce the flow of bone fluid; allowing the bone fluid to bleed through the at least one perforation up into the cartilage defect to fill at least a portion of the cartilage defect; and applying a biomaterial into the defect to produce a clot for cartilage regeneration.

In this embodiment, the biomaterial may be applied to the defect after bone fluid bleeds into the defect to fill at least a portion of the defect. The biomaterial may be a surgical hemostat, wherein the hemostat includes thrombin and collagen.

In a further embodiment, the present invention includes a method for creating a healing matrix for a cartilage defect in-situ including the steps of preparing a cartilage defect by removing unwanted or damaged tissue; creating at least one perforation into or through subchondral bone below and/or adjacent to the cartilage defect to induce the flow of bone fluid; allowing the bone fluid to bleed through the at least one perforation up into the cartilage defect to fill at least a portion of the cartilage defect; and applying a biomaterial into the defect area to produce a clot for cartilage regeneration. The interaction of the biomaterial and the bone fluid may form an enhanced clot. The biomaterial may be a surgical hemostat which may include thrombin and collagen.

In still a further embodiment, the present invention includes a kit for repairing a cartilage defect including a bone marrow stimulation instrument comprising at least one drill guide and a drill and a biomaterial. The biomaterial may be a surgical hemostat which may include collagen and thrombin. The kit may further include a cap adapted to prevent migration of bone fluid, migrating into the cartilage defect through perforations in subchondral bone below and/or adjacent to the cartilage defect formed by the bone marrow stimulation instrument, away from the cartilage defect.

BRIEF DESCRIPTION OF THE DRAWINGS

FIGS. 1A-B illustrate one embodiment of preparing a tissue defect, specifically a cartilage defect.

FIGS. 2A-B illustrate one embodiment of creating at least one perforation into or through subchondral bone.

DETAILED DESCRIPTION

The various embodiments of the invention can be used to repair cartilage in any patient in need thereof. By "patient" it is meant any organism which has cartilage, including, but not limited to humans, sheep, monkeys, horses, goats, dogs, cats, and rodents. Unless otherwise stated, the various exemplary embodiments herein are described in terms of the patient being a human.

The various embodiments disclosed herein may be used in defect sites throughout the body including but not limited to defect sites in the various joints of the body such as the knee, hip, ankle, shoulder, elbow, finger, wrist, toe, temporomandibular, sternoclavicular, zygapophyseal, or the like. Similarly, the various embodiments of the present invention may also be used in other areas of the human body where cartilage and subchondral bone are found, including but not limited to the ribs, vertebral column, pelvis, and the like.

The term "in-situ," as used herein, is defined as being in the body of the patient during surgery. For example, as used herein with regard to certain embodiments of the present invention, when something is in-situ it is in position within the patient, and more particularly, in the surgical site within the patient, during the surgical procedure or following the surgical procedure.

As such, it should be understood that the embodiments discussed herein are merely exemplary in nature and is in no way intended to limit the invention, its application, or uses. For example, although the present teachings are illustrated for repairing tissue defects, the present teachings can be used to repair and facilitate healing or regeneration of any injured tissue, and particularly other avascular tissues. However, for ease of discussion, the following embodiments of the present invention are described with reference to cartilage, and in particular hyaline cartilage including articular cartilage, such as in the knee joint, and the underlying and/or adjacent subchondral bone. Similarly, while the exemplary methods described below are intended to be used with arthroscopic techniques, mini-open and open surgery may also be performed using these methods. Moreover, if performed arthroscopically, a surgical cannula may be used as is known.

In one embodiment, the present invention includes a method for repairing a cartilage defect including the steps of preparing a cartilage defect by removing unwanted or damaged tissue, creating at least one perforation into or through the subchondral bone, below and/or adjacent the cartilage defect, to induce the flow of bone fluid, allowing the bone fluid to bleed through the at least one perforation up into the cartilage defect to fill at least a portion of the cartilage defect, and applying a biomaterial into the defect area to produce a clot for cartilage regeneration.

Figure 1A:
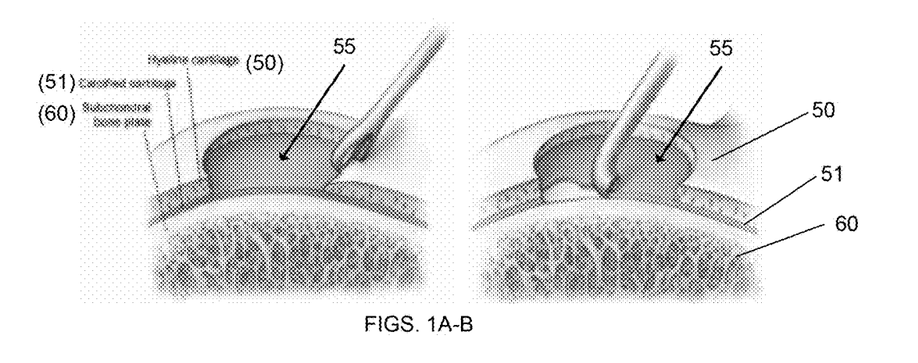

The step of preparing the cartilage 50, as illustrated in FIGS. 1A-B, refers to cleaning the defect 55 by removing unwanted soft tissue including damaged tissue and dead tissue to create a clean and smooth defect area, as is known in the art. The cartilage defect 55 is typically debrided to remove damaged cartilage tissue and prepare the edges of the cartilage defect to maximize repair and integration of the clot. Optionally, the calcified cartilage layer may be removed to expose the subchondral bone 60 below and/or adjacent to the cartilage defect site 55 which may maximize bone marrow stimulation, discussed below.

The step of creating at least one perforation 65 is generally referred to as "bone marrow stimulation" and is defined generally as any technique which causes bleeding (e.g., the flow of bone fluid) in the subchondral bone 60. For example, bone marrow stimulation is generally performed by creating at least one perforation 65 into or through the subchondral bone 60, using a technique such as microchanneling, microfracture, microdrilling, or the like. Any of these techniques, or similar techniques, create channels or openings in the subchondral bone through which "bone fluid" may migrate or flow from the bone, through the channels or openings, and into the cartilage defect site, for example. The bone fluid may include, for example, blood, bone marrow, cells, plasma or any combination of these components.

Figure 2A:
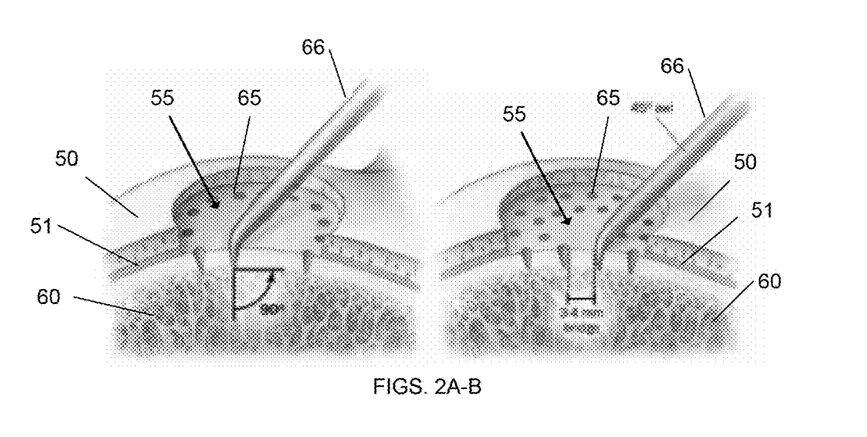

FIGS. 2A-B illustrate one example of bone marrow stimulation referred to as microfracture. As illustrated, the cartilage defect 55 is accessed and prepared, as discussed above, and then an awl 66 or similar sharp-tipped instrument is used to form at least one perforation 65 into and/or through the subchondral bone 60. Commonly, a hammer or mallet is used to punch the sharp tip of the awl into or through the subchondral bone. In this example, the perforations cover most if not the entire surface area of the subchondral bone below the cartilage defect site and are set about 1 mm to about 5 mm apart, preferably about 2 mm to about 4 mm apart, and more preferably about 3 mm to about 4 mm apart, from one another, though any desired configuration may be formed, so long as sufficient bone mass, or "bone bridges," are maintained between perforations to preserve the integrity of the subchondral bone. Of course, additional perforations adjacent the defect site, such as through adjacent cartilage and into subchondral bone below such adjacent cartilage, may also be performed, though it may be preferable in most instances to limit the damage to adjacent, presumably healthy, cartilage.

In certain embodiments, such as is illustrated, for example, in FIGS. 3A, 3B, 5A, 5B, bone marrow stimulation may be performed using a technique known as microdrilling, in which a drill is used to form the at least one perforation into or through the subchondral bone beneath and/or adjacent to the cartilage defect site. One such example of microdrilling methods and instrumentation is disclosed in U.S. application Ser. No. 13/368,730, published as U.S. Published App. No. 2012/0203231 and filed Feb. 8, 2012, the entirety of which is incorporated by reference herein as if fully set forth herein. One such microdrilling system suitable for bone marrow stimulation, and which is intended to be used in conjunction with the present invention, is the MicroFX™ OCD Osteochondral Drill System (Stryker Endoscopy, Stryker Corp., Kalamazoo, Mich.).

Figure 3A:
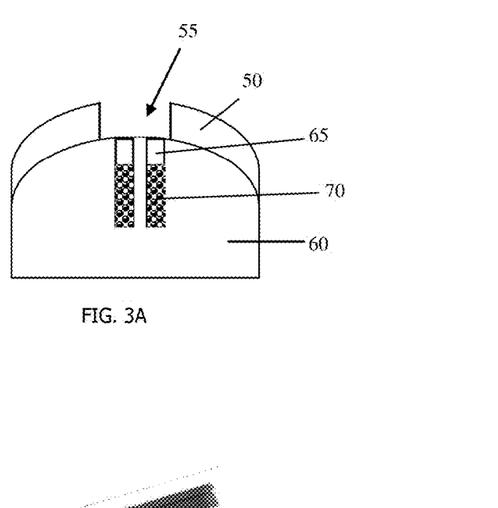
FIGS. 3A-B illustrate one embodiment of bone fluid bleeding through the at least one perforations, illustrated in FIGS. 2A-B, and into the prepared cartilage defect, illustrated in FIGS. 1A-B.
Figure 3B:
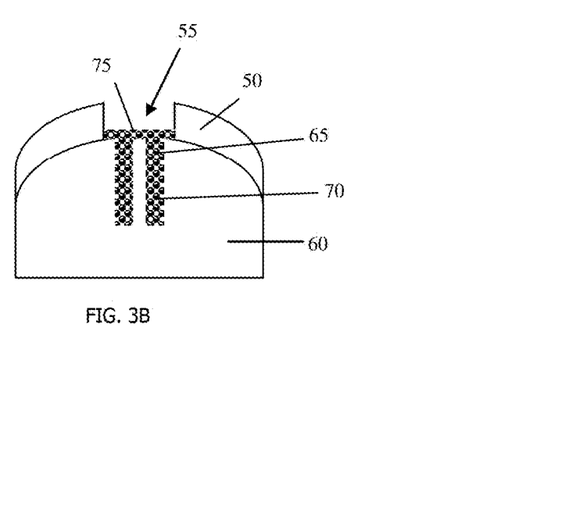

As illustrated in FIGS. 3A-B, following the creation of the at least one perforation into or through the subchondral bone 60, bone fluid 70 is allowed to bleed through the at least one perforation 65 and up into the cartilage defect 55, such that the operator may observe bone fluid migrating into the cartilage defect forming a bloody bed 75 in at least a portion of the defect 55. This may be done by allowing the bleeding to naturally occur, providing a "negative pressure" to pull the bone fluid into the cartilage defect, or otherwise promoting the bleeding into the cartilage defect. For example, at the onset of the surgical procedure, a tourniquet (not shown) may be placed proximal to the cartilage defect (e.g., if the defect is in the knee, the tourniquet would be placed along the length of the femur above the knee) to restrict or even inhibit blood flow to the defect site. Following bone marrow stimulation, the tourniquet may be loosened or removed to allow uninhibited bleeding up into the cartilage defect such that the bone fluid fills at least a portion of the cartilage defect, and such that the operator can observe bone fluid migrating into the cartilage defect, forming a bloody bed 75. Alternatively, if no tourniquet is used, as the perforations are formed, such bleeding may occur immediately, or soon after completion of the perforation, such that uninhibited bleeding up into the cartilage defect occurs and at least a portion of the defect fills with bone fluid to form the bed 75.

Preferably, the bone fluid 70 is permitted to fill at least a portion of the cartilage defect, forming the bloody bed 75, as in FIG. 3B. The percentage of fill by the bone fluid 70 of the cartilage defect site 55 is largely dependent on the quality of the perforations 65 and whether largely uninhibited bleeding is permitted through the perforations. As such, it is preferred that the perforations be created by a microdrilling procedure as such perforations are typically better formed, and the porosity of the bone around each perforation is typically preserved, relative to perforations made by other procedures, such as microfracture (as in FIGS. 2A-B). However, as discussed further below, it is preferable that the bone fluid entering the defect 55 not be so much as to substantially, if not completely, fill the defect as this may result in insufficient volume in the defect 55 for placement of the biomaterial 10.

Figure 4:
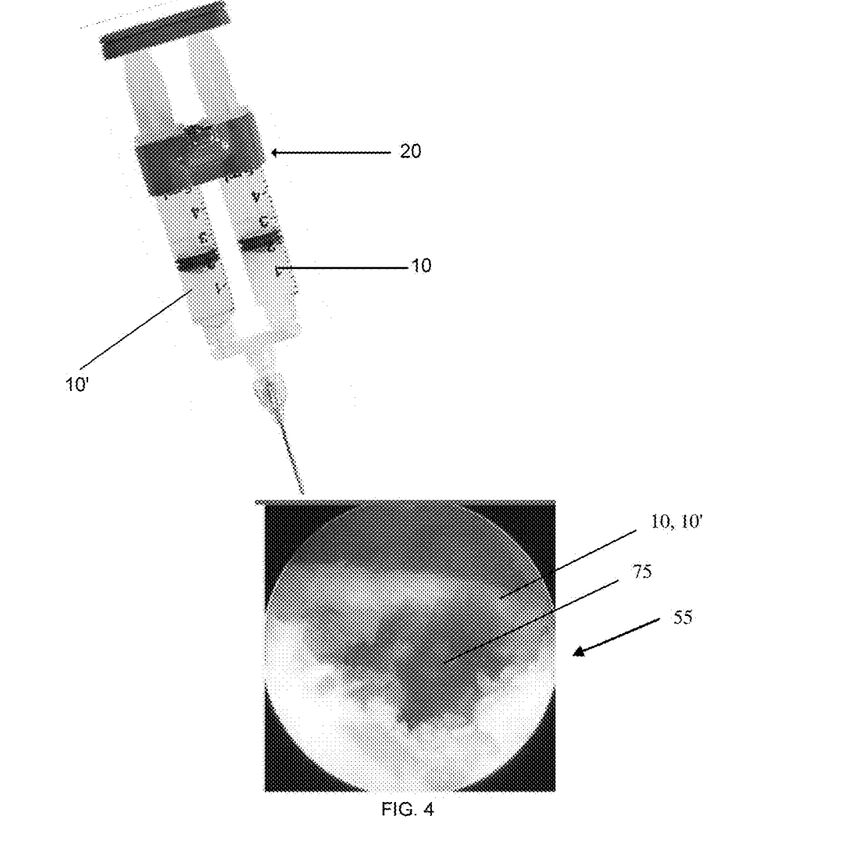
FIG. 4 illustrates one embodiment of a biomaterial applicator applying biomaterial to the cartilage defect partially filled with bone fluid, as illustrated in FIG. 3B.

As such, continuing with this embodiment, as depicted in FIG. 4, the present invention includes the step of applying a biomaterial 10,10' (while a two-part biomaterial is illustrated, a single-part biomaterial 10 may alternatively be used) into the defect area 55 to produce a clot for cartilage regeneration. As depicted in FIG. 4, the biomaterial 10,10' may be applied to the defect area 55 in-situ, once bleeding into the defect site (forming the bloody bed 75) has already been observed and has filled at least a portion of the defect site, through the use of a syringe 20, though other applicators such as spray applicators, vials, sponges, pouring containers, catheters, cannulas, tubes, funnels or the like may also be used. Alternatively, if the biomaterial is in solid form (not shown), the biomaterial may be merely placed within the cartilage defect using an appropriate instrument. The biomatrial may also be in other forms such as powder, granular, in morsels, putty, gel, flowable form, or the like. In one embodiment in which the biomaterial is in solid form, upon contact with the bone fluid, the biomaterial softens or solubilizes to mix with the bone fluid.

Figure 5A:
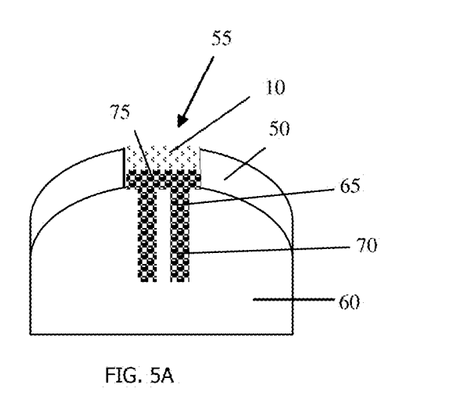
FIG. 5A illustrates the applied biomaterial in the cartilage defect interacting and mixing with the bone fluid.
Figure 5B:
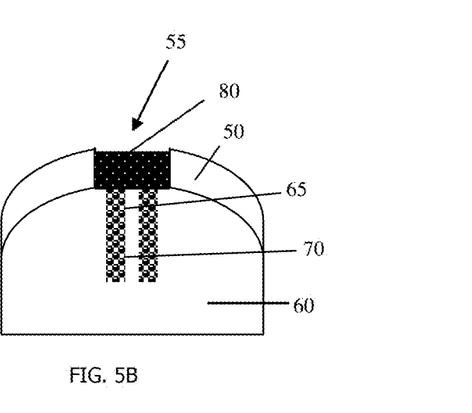
FIG. 5B illustrates an enhanced clot created by the interaction of the applied biomaterial and the bone fluid in the cartilage defect.

As illustrated in FIG. 5A, upon application of the biomaterial 10 to the cartilage defect site 55, the biomaterial 10 and bone fluid 75 are intended to substantially completely fill, if not completely fill, the defect site 55. The resulting interaction of the biomaterial with the bone fluid within the cartilage defect, through intermixing or the like, may result in an "enhanced clot" 80 within at least a portion of the defect site, as illustrated in FIG. 5B. As used herein, an enhanced clot 80 is defined as a clot, which over time, regenerates into cartilage tissue similar in nature to native cartilage 50. The enhanced clot of the present invention is formed in-situ, upon application of the biomaterial 10 into the cartilage defect 55 such that it interacts and mixes with the bone fluid 75 which migrates into the defect site 55.

In some embodiments, the ratio of the amount of biomaterial 10 injected into the bone fluid 75 in the cartilage defect site 55 is 1:1, as illustrated in FIG. 5A, for example. In other embodiments, the ratio of the amount of biomaterial injected into the bone fluid in the cartilage defect site is 2:1. Still other embodiments may have a ratio of 1:2. Of course, other ratios of biomaterial to bone fluid, which migrated into the cartilage defect area, are also envisioned.

It is preferred that the biomaterial 10 be limited to remain only within the defect site 55 such that it does not migrate into the at least one perforation 65 as it is an aspect of the present invention that the biomaterial, and thus the enhanced clot 80, remain only in the volume of the cartilage defect 55. However, as the biomaterial interacts and mixes with the bone fluid 75, it is foreseeable that a portion of the biomaterial may migrate into at least one of the perforations, such that the enhanced clot may extend into such perforation or perforations. However, in performing this method, it is envisioned that an amount of biomaterial is used that is sufficient only to form a clot within the cartilage defect, such that the amount of biomaterial is insufficient to reach the perforations before it interacts with the bone fluid within the defect 55 and clots.

Thus, once the clot 80 is formed within the cartilage defect 55, the perforations 65 may remain at least partially open for a period of time such that additional bone fluid 70, or at least nutrients found in the bone fluid, may continue to migrate from the bone, through the perforations, and into the cartilage defect, though such migration may be somewhat reduced with time. Once in the cartilage defect, this continued migration may move through the matrix formed by the clot 80 to replenish nutrients within the defect 55. Alternatively, in another mechanism of healing where the clot 80 effectively operates as a patch or covering (e.g., where the clot 80 remains generally on the surface of the bone fluid 75 within the defect 55), such migration of nutrients and/or bone fluid may remain under the formed clot 80 to interact with the cartilage defect 55. In any event, following formation of enhanced clot 80, nutrients found in the bone fluid may continue to be replenished by continued flow of bone fluid through the perforations (though potentially at a reduced rate) which may enhance cartilage regeneration. Of course, with time, the bone fluid within the perforations will gel and clot on its own, though it is an aspect of the present invention that the biomaterial should not contribute to this clotting process. As such, another aspect of this embodiment is that this method does not require the use of implants or substrates to fill the at least one perforations in the subchondral bone, but rather, this method may rely on the natural clotting abilities of the bone fluid itself to form a clot within the perforations.

Additionally, after the clot 80 is formed, and the cartilage defect 55 begins to heal, the synovial fluid of the joint (e.g., the knee) may also provide additional nutrients to the defect site 55 through the migration of such nutrients through the matrix of the clot 80 in the defect 55.

Figure 6:
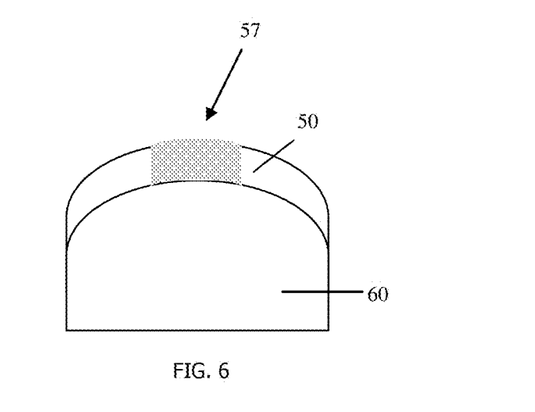
FIG. 6 illustrates on example of a healed cartilage defect.
Figure 7:
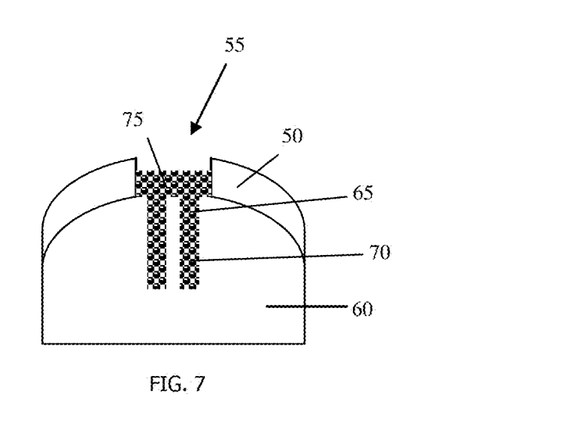
FIG. 7 illustrates a cartilage defect containing bone fluid, where no biomaterial is applied.

As illustrated in FIG. 6, the enhanced clot of the present invention promotes the formation of cartilage 57 over a period of time that resembles native cartilage in terms of structure, integrity and composition in such a manner so that it is indistinguishable from the native cartilage 50. This enhanced clot (illustrated in FIG. 5B) is superior to the clot that is formed in typical defect repair procedures, such as a traditional microfracture repair as illustrated in FIG. 7, in which the clot is not enhanced and therefore will not appear similar in nature to native cartilage but is instead fibrous and lacking in adequate strength necessary for a long-term repair. Further, in typical current procedures, implants or biological materials are placed in the defect that result in an inferior clot and thus create fibrous, inferior, tissue over time.

In one embodiment, the biomaterial 10 itself of the present invention may be any biological material capable of, upon interacting with the bone fluid, controlling bleeding, forming an enhanced clot, and over time forming tissue similar in nature to native cartilage. Exemplary biomaterials may be a surgical hemostat, or a biological material including components such as thrombin, autologous thrombin (i.e., prepared using the patient's own blood), collagen, platelets, plasma, fibrinogen, fibrin starch microspheres, bone marrow, bone marrow plasma, bone marrow derived cells, and the like, or any combination. The biomaterial may be in liquid or gel form, suitable for injection, spray, or other applications. Alternatively, the biomaterial may also be in solid form and may have a shape suitable for insertion into the defect site, such as cylindrical, matrix, sponge, pad, film, sheet, or the like. Of course, if the biomaterial is in solid form, the biomaterial may be cut, folded, or otherwise manipulated into a shape suitable for insertion into the defect site and, preferably, to substantially completely fill, if not completely fill, the defect site along with the bone fluid. For example, if the biomaterial is in solid form, upon contact with the bone fluid, the biomaterial may soften or solubilize to mix with the bone fluid.

One exemplary biomaterial for use with the present invention is Stryker Orthobiologics' Vitagel® Surgical Hemostat (manufactured by Orthovita, Inc., Malvern, Pa.). Vitagel® Surgical Hemostat is an injectable hemostat which includes thrombin and collagen, as well as additional additives such as a buffer and the like. Vitagel® Surgical Hemostat may have properties suitable to both control bleeding and facilitate healing, while also interacting with the bone fluid to assist in creating an enhanced clot thereby regenerating cartilage akin to native cartilage. Other suitable biomaterials may be used in the present invention such as those disclosed in U.S. Pat. Nos. 5,290,552; 6,096,309; 6,110,484; 6,277,394; 5,752,974; 5,616,689; 5,024,841; 5,997,811; and 5,110,604, each of which is incorporated by reference herein as if fully set forth herein.

In another embodiment, particularly efficacious surgical hemostats may be used to practice the present invention which can be formulated by combining thrombin together with microfibrillar collagen. The microfibrillar collagen acts to improve the functionality of the hemostat, and also plays an important role in the kinetics of fibrin clot formation, as well as the overall physical characteristics of the fibrin clot. The thrombin can be derived from a variety of natural sources, such as from pooled animal plasma. For example, bovine thrombin is readily available from a wide variety of commercial sources. In addition, recombinant thrombin can be utilized, which may be synthesized from a variety of recombinant sources such as transformed host (bacterial, yeast or mammalian) cells, or specifically from human cells. In addition, thrombin-like compounds such as certain proteolytic snake venoms, as well as thrombin precursors such as prothrombin can also be used as the source of thrombin for use in the present invention. Alternatively, the thrombin may be derived from autologous or allogenic plasma.

Such microfibrillar collagen which is useful in this embodiment may have an average fibril diameter of about 3 nm to about 30 nm and a melting temperature as determined using differential scanning calorimetry between about 42° C. to about 46° C.

In yet another embodiment, the surgical hemostat formulation may include various forms of collagen, either individual or in combination. For example, the hemostat may include Type I collagen, Type II collagen, or a combination of both types of collagen. In another example, the hemostat includes only Type II collagen. The inclusion of Type II collagen may be important as Type II collagen is generally found in native cartilage tissue, and thus, the inclusion of Type II in the hemostat, applied to the defect, may result in the growth of tissue similar to the surrounding native cartilage tissue. The inclusion of Type II collagen can have the additional benefit of better binding with the surrounding native cartilage tissue than if Type I collagen (as found in bones, scar tissue, and the like) is used in the hemostat. This improved binding may also provide a better clot which effectively "seals" the defect such that, once the clot is formed, migration of bone fluid away from the defect site, and around the clot, is minimized if not altogether halted.

Further to this embodiment, the surgical hemostat formulation may further include additional components. In one particular example, the formulation may further include calcium ions, which may be added to increase the effective calcium ion concentration at the site of application to an amount which will provide for adequate clot formation. When used at sites having sufficient endogenous calcium ions present, it is not necessary for calcium ions to be added. However, calcium ions are effective at promoting microfibril formation from fibrillar collagen. Accordingly, if the surgical hemostats of the present invention are formed from fibrillar collagen, it is desired to add sufficient calcium ions to the hemostat to form microfibrillar collagen.

In a further example of a suitable surgical hemostat formulation of the present invention, polyethylene glycol (PEG) may be included to stabilize thrombin. The PEG can be of any suitable molecular weight, such as about 1,000 to about 8,000. Additionally, the PEG can be present in a wide range of concentrations, such as about 0.1 to about 2%, but is preferably present at a concentration of about 0.1 to about 0.3%.

In yet a further example of a suitable surgical hemostat formulation of the present invention, the formulation including a thrombin plus microfibrillar collagen may further include a source of fibrinogen. The fibrinogen can be added directly to the formulation, or it can be supplied as a separate component in an aqueous medium. A preferred aqueous medium comprising fibrinogen is plasma, and more preferably, it is human plasma, and most preferably it is autologous plasma. In certain embodiments, the formulation including thrombin plus microfibrillar collagen may be mixed with the bone fluid at the cartilage defect site. In another aspect of the invention, a suspension of platelets can be used in conjunction with the thrombin plus microfibrillar collagen formulation, since platelets are activated by thrombin, which may initiate the clotting cascade and can effect fibrin clot formation in the absence of exogenously supplied fibrinogen. In yet another aspect of the invention, the thrombin plus microfibrillar collagen formulation may be combined with bone marrow aspirate or concentrated bone marrow aspirate.

In another example of a suitable surgical hemostat formulation of the present invention, the hemostat may include collagen that is in the form of a mixture of microfibrillar and non-microfibrillar fibrillar collagen. What is intended by the term non-microfibrillar fibrillar collagen is collagen having fibrils that are larger than microfibrils. In particular, hemostats having mixtures of microfibrillar collagen and non-microfibrillar fibrillar collagen in a ratio of at least 1:1 (w/w), respectively, may be useful for certain applications. For example, mixtures of microfibrillar collagen and fibrillar collagen with larger fibril sizes may be more flowable and thus easier to use in spraying applicators.

In still another example, the surgical hemostat may include methylated collagen which may be a suitable form of collagen if administered to a cartilage defect site at which it may interact with intrinsic plasma proteins.

Other disassembly agents which can be included for the purpose of converting fibrillar to microfibrillar collagen may include, but are not limited to, glycerol, sucrose and related polyols, such as maltose, sorbitol and mannitol.

The inclusion of hydrophilic polymers such as polyalkyl oxides, preferably polyethylene glycol (PEG), in such thrombin-based surgical hemostats may serve to stabilize the thrombin by inhibiting thrombin-thrombin interactions, which prevents autocatalysis. Additional stabilizers may include sugars (e.g. sorbitol, mannitol, glucose, sucrose) and amino acids (e.g. glycine) such as those described in EPO 478,827A1; EPO 302,754B1; and GB 2,041,942A, all of which are incorporated by reference herein as if fully set forth herein. Still other means for stabilizing thrombin are described in U.S. Pat. Nos. 5,219,328; 5,318,524; and 5,407,671, all of which are incorporated by reference herein as if fully set forth herein.

Unlike other procedures known in the art, the biomaterial of the present invention is not coated onto the bone or placed within the defect site or bone prior to the initiation of bleeding up into the defect site. Rather, the biomaterial of the present invention is applied to the cartilage defect site once the defect site is at least partially filled with bone fluid. The biomaterial may be applied multiple times as necessary in order to limit bleeding from the defect site (i.e., prevent overflow of bone fluid, and biomaterial, from the defect site) and/or to create a suitable enhanced clot to ensure proper cartilage regeneration. The biomaterial may further be applied after bleeding has spread over the cartilage defect and the adjacent cartilage surface (i.e., the bone fluid has overflowed the cartilage defect) in order to facilitate healing and prevent adhesions, though such an instance is not preferred as there is no open volume in the defect for placement, and containment, of the biomaterial. However, care must be taken to minimize the chance of intrusion by the biomaterial into the at least one perforations, as discussed above. Thus, the amount of biomaterial applied to the cartilage defect depends on the volume of the defect, the amount of bone fluid which migrates into the defect and the clotting ability of the bone fluid itself. For example, at least 10% of the volume of the defect should be available, following bleeding into the defect, for the application of the biomaterial, and preferably 50% or more of the volume should be available. However, it is conceivable that up to 90% of the volume of the defect, or even 100% of the volume of the defect, may be available for the application of the biomaterial. Likewise, the timing of the application of the biomaterial is largely dependent on the time required for the bleeding to commence and for at least a portion of the cartilage defect to fill with bone fluid.

This method may be performed on multiple cartilage defect sites, within the same joint or within multiple joints, within a single patient. Further, this method may be used on cartilage defect sites of any size.

In another embodiment, the present invention includes a method for enhancing clot formation and/or regenerating cartilage within a cartilage defect site, the method including accessing and preparing the cartilage defect site, creating at least one perforation into or through the subchondral bone to induce the flow of bone fluid, allowing the bone fluid to bleed through the at least one perforation up into the cartilage defect to fill at least a portion of the cartilage defect, and applying a biomaterial into the defect area to produce an enhanced clot for cartilage regeneration. In this embodiment, the bone fluid, which at least partially fills the defect site, and the biomaterial applied to the defect, together may substantially completely fill, or alternatively, completely fill, the cartilage defect site.

In a further embodiment, the present invention includes a method for creating a healing matrix for a cartilage defect in-situ, the method including preparing a cartilage defect by removing unwanted or damaged tissue, creating at least one perforation into or through the subchondral bone below and/or adjacent the defect to induce the flow of bone fluid, allowing the bone fluid to bleed through the at least one perforation up into the cartilage defect to fill at least a portion of the cartilage defect, and applying a biomaterial into the defect area to produce a clot for cartilage regeneration. The biomaterial may be a surgical hemostat, as discussed above and may further be a surgical hemostat including thrombin and collagen. As discussed above, the interaction of the biomaterial and the bone fluid forms an enhanced clot.

In a further embodiment, the present invention may also include a method of providing instructions or information to practice any of the various methods of cartilage or tissue repair surgery described herein. For example, the method may include supplying a surgical protocol, or like document, to provide step-by-step instructions for performing any of the method embodiments of the present invention.

Other embodiments of methods of repairing a defect in tissue are also envisioned which are suitable in obtaining an enhanced clot within the tissue defect. Any of the above disclosed methods, while described based on a cartilage defect, may also be used to repair other defects in other types of tissue, particularly other avascular tissues.

In another embodiment, the present invention includes a kit for achieving the various present invention methods. In one embodiment, the kit includes sterile instruments for use in a surgical environment including at least one sterile instrument for making at least one perforation into or through subchondral bone, and a sterile biomaterial or surgical hemostat. In some embodiments, the instrument can be a drill, a flexible drill and curved drill guide (as in U.S. application Ser. No. 13/368,730, incorporated by reference herein), an awl, a pick or any similar sharp-tipped apparatus or combination of instruments; and the biomaterial can include, for example, collagen and thrombin, though other biomaterials may also be used. The kit may include additional instruments such as a biomaterial applicator, as described above (see FIG. 4, for example), and a cap, as discussed below.

In a further embodiment, the present invention includes a kit for repairing a cartilage defect, the kit including a microchanneling instrument for performing bone marrow stimulation, as discussed above, wherein the microchanneling instrument may include at least one drill guide and a drill. The kit also includes a biomaterial and may also include an applicator for the biomaterial. The applicator may be syringe 20 (see FIG. 4) or may be a spray applicator or the like. The biomaterial may include a surgical hemostat which includes collagen and thrombin.

The drill of this embodiment may be a standard rigid drill coupled with a straight guide or may be a flexible drill coupled with a curved drill guide. The kit may alternatively include a plurality of curved drill guides having various degrees of curvature, for use with the flexible drill, which may be selected by the operator as a predetermined angle of curvature based on the type of surgery, location of surgery, surrounding anatomy, angle of approach to the surgical site, and the like.

Figure 8A:
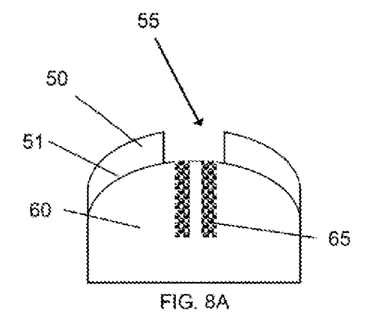
FIGS. 8A-D illustrate another embodiment of a method of repairing a cartilage defect including the use of a cap.
Figure 8B:
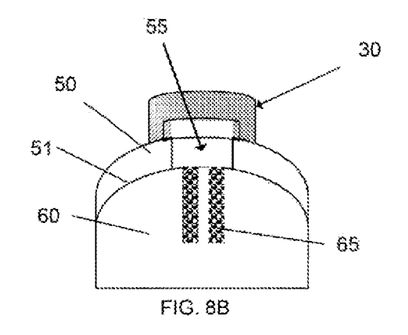

As illustrated in FIGS. 8A-D, the kit may also include a cap 30. The cap may be adapted to prevent migration of bone fluid, migrating into the cartilage defect 55 through perforations 65 in subchondral bone 60 below and/or adjacent to the cartilage defect (see FIG. 8A) formed by the bone marrow stimulation instrument, away from the cartilage defect. In use, the cap 30 may be positioned after the at least one perforations have been formed into or through the subchondral bone. For example, as bleeding occurs, the amount of bone fluid which migrates through the perforations may be greater than the volume of the cartilage defect such that the bone fluid may overflow from the defect site and contact the surrounding healthy cartilage, or otherwise migrate away from the defect site. The cap may be positioned, as illustrated in FIG. 8B, such that the bone fluid is prevented from migrating out of the cartilage defect.

Figure 8C:
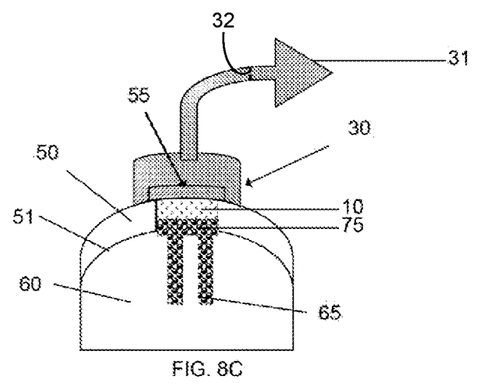

Similarly, as illustrated in FIG. 8C, the cap 30 may also be kept in position as the biomaterial 10 is added to the defect site 55 through a cannulation 31 in the cap. In this instance, the cap may contain both the bone fluid 75 and the biomaterial 10 at the defect site such that the clot may be concentrated within the defect site. In using the cap, the cap assists in providing a wet environment (i.e., limiting contact with the surrounding air, containing bone fluid at defect site, etc.) for application of the biomaterial. Similarly, when used in arthroscopic applications, the cap may provide protection to the bone fluid and biomaterial to prevent them from washing away in the saline surrounding the defect site. The cap may further assist in preventing the clot from migrating, blistering, or breaking away from the defect site. Further, the cap may be rigid or flexible. For example, the cap may be flexible enough to depress the defect site thereby forming a depression in the clot such that the depression of the clot can be flush to or slightly below the surrounding cartilage surface. Similarly, the cannulation 31 may be used to extract excess bone fluid from the cartilage defect site in the event of excess bleeding, difficulty obtaining a clot, a decision by the operator to flush bone fluid through the cartilage defect (e.g., maintain a flow of bone fluid), or the like. The cannulation 31 may merely be an opening through which excess bone fluid may drain, or alternatively, the cannulation 31 may be connected to a pump, or the like, to create a negative pressure or suction which may actively draw the bone fluid from the cartilage defect, into the cap and out through the cannulation 31. In yet another alternative, the cannulation 31 may also include a filter 32 which allows the extrudate to flow through the filter 32 and out the cannulation while the cells, platelets, nutrients and other biological agents in the bone fluid are kept within the cap, which may concentrate these components in the cartilage defect, which may result in better cartilage growth, and thus a better repair.

Figure 8D:
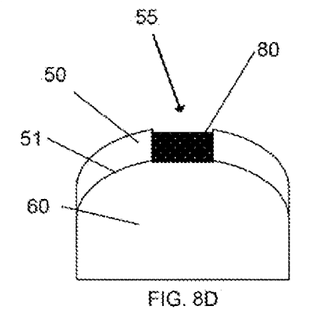

FIG. 8D illustrates the final enhanced clot 80, formed within the cartilage defect 55. Once the clot is stabilized, the cap may be removed, as illustrated in FIG. 8D. Also, as illustrated in FIG. 8D, over time, the perforations in the subchondral bone may heal themselves.

In another embodiment, the present invention may include a kit including the MicroFX™ OCD Osteochondral Drill System and the Vitagel® Surgical Hemostat biomaterial. These two products may be sold together or sold separately and later combined as a kit by the operator.

Example 1

The present invention methods were evaluated in an ovine cartilage defect model. Twenty-four skeletally mature castrated male sheep (inclusive of four spare animals) were utilized to confirm that the addition of a hemostat mixed with local bone fluid (from marrow stimulation) in a cartilage defect would produce an enhanced clot in comparison to bone fluid without a hemostat. Animals were evaluated immediately following surgery (t=0 weeks (wks)), after 2 weeks (t=2 wks) and at 6 months (t=24 wks).

A sheep articular cartilage repair model using microdrilling bone marrow stimulation was utilized for this study. A rubber bandage serving as a tourniquet was applied to the limb, distal to the cartilage defects to be created, to further promote the flow of bone fluid and subchondral bleeding. Two cartilage defects, full thickness chondral defects, were created through small knee arthrotomies in each animal knee: 1) on the medial condyle, central load-bearing region, and 2) on the trochlea, lateral distal facet. Defects were created using metal templates to delineate the removal of cartilage: 8 mm×10 mm in size for the condyle, 6 mm×12 mm in size for the trochlea. Defects were microdrilled with 2.1 diameter holes (11 mm deep), spaced by approximately 2 mm. Four perforations/prepared channels were created in the trochlea defect (Z pattern), five in the condyle defect (X pattern). The prepared channels were created using the MicroFX™ OCD Osteochondral Drill System (2.1 mm diameter drill, with modified guide to drill to 11 mm depth) and were of sufficient depth to ensure penetration of the subchondral plate and communication with the marrow. Fatty droplets were seen to emanate from the channel apertures to confirm that adequate depth was achieved.

Bleeding of the defect occurred with alternating condyle and trochlear defects being treated. For the test group, defects were treated in accordance with the present invention method utilizing a hemostat (Vitagel® RT Surgical Hemostat, Vitagel® including human recombinant thrombin, prepared per the manufacturer's Instructions for Use (Stryker Orthobiologics, Orthovita, Malvern, Pa.)) to mix with the bone fluid until the defect was filled ("Vitagel+ MDr"). In the control group, a standard microdrilling/microfracture method was used and Vitagel was not applied to the defects ("MDr") (e.g., control defects were left bleeding and contained only bone fluid). Clots were deemed "formed" when the defect was filled or bleeding had stopped before the defect was filled. Test and control treatment were conducted in alternating fashion according to the scheme outlined in Table 1.

TABLE 1

Animal Groups and Study Design

| Animal | Live Phase Duration | Knee | Condyle | Trochlea |
|---|---|---|---|---|
| 1 | t = 0 wks | Left | Vitagel + MDr | MDr |
|  |  | Right | MDr | Vitagel + MDr |
| 2 | t = 0 wks | Left | MDr | Vitagel + MDr |
|  |  | Right | Vitagel + MDr | MDr |
| 3 | t = 0 wks | Left | Vitagel + MDr | MDr |
|  |  | Right | MDr | Vitagel + MDr |
| 4 | t = 0 wks | Left | MDr | Vitagel + MDr |
|  |  | Right | Vitagel + MDr | MDr |
| 5 | t = 2 wks | Left | Vitagel + MDr | MDr |
| 6 | t = 2 wks | Right | MDr | Vitagel + MDr |
| 7 | t = 2 wks | Left | MDr | Vitagel + MDr |
| 8 | t = 2 wks | Right | Vitagel + MDr | MDr |
| 9 | t = 2 wks | Left | Vitagel + MDr | MDr |
| 10 | t = 2 wks | Right | MDr | Vitagel + MDr |
| 11 | t = 2 wks | Left | MDr | Vitagel + MDr |
| 12 | t = 2 wks | Right | Vitagel + MDr | MDr |
| 13 | t = 24 wks | Left | Vitagel + MDr | MDr |
| 14 | t = 24 wks | Right | MDr | Vitagel + MDr |
| 15 | t = 24 wks | Left | MDr | Vitagel + MDr |
| 16 | t = 24 wks | Right | Vitagel + MDr | MDr |
| 17 | t = 24 wks | Left | Vitagel + MDr | MDr |
| 18 | t = 24 wks | Right | MDr | Vitagel + MDr |
| 19 | t = 24 wks | Left | MDr | Vitagel + MDr |
| 20 | t = 24 wks | Right | Vitagel + MDr | MDr |
| 21-24 |  |  | Spare Animals |  |

Time from hemostat application to time of hemostasis was recorded to the nearest second. The amount of hemostat used was also recorded (volume of preparation volume remaining after application). Upon study completion, pathological observations and histological analyses will be presented.

At the time of sacrifice for the 6-month animals, the repaired defect will be left intact for further analysis. Additional evaluations will include biochemistry, integrity/structure, histology, gene expression, composition, integration, defect fill and subchondral bone structure measurements. The animal model and evaluations are partially based on the work conducted by Hoemann et al., "Chitosan-glycerol phosphate/blood implants improve hyaline cartilage repair in ovine microfracture defects", *JBJS,* 87-A (12): 2671-2686 (2005) and Marchand et al., "Solidification mechanisms of chitosan-glycerol phosphate/blood implant for articular cartilage repair", *Osteoarthritis and Cartilage,* 17: 953-960 (2009).

Figure 9:
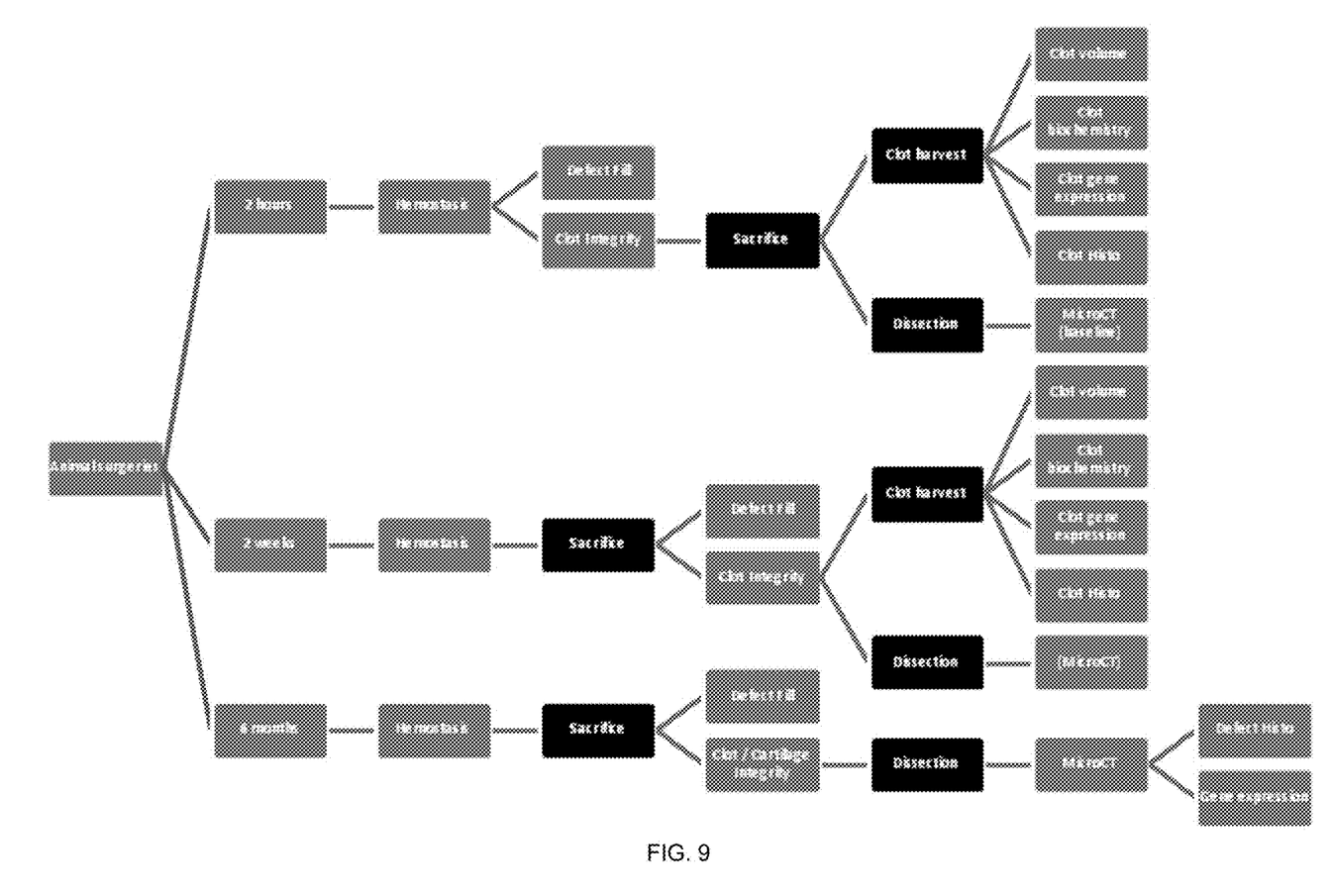
FIG. 9 is a chart illustrating the sequence of sample preparation and sample analysis for use in illustrative Example 1.
Figure 10A:
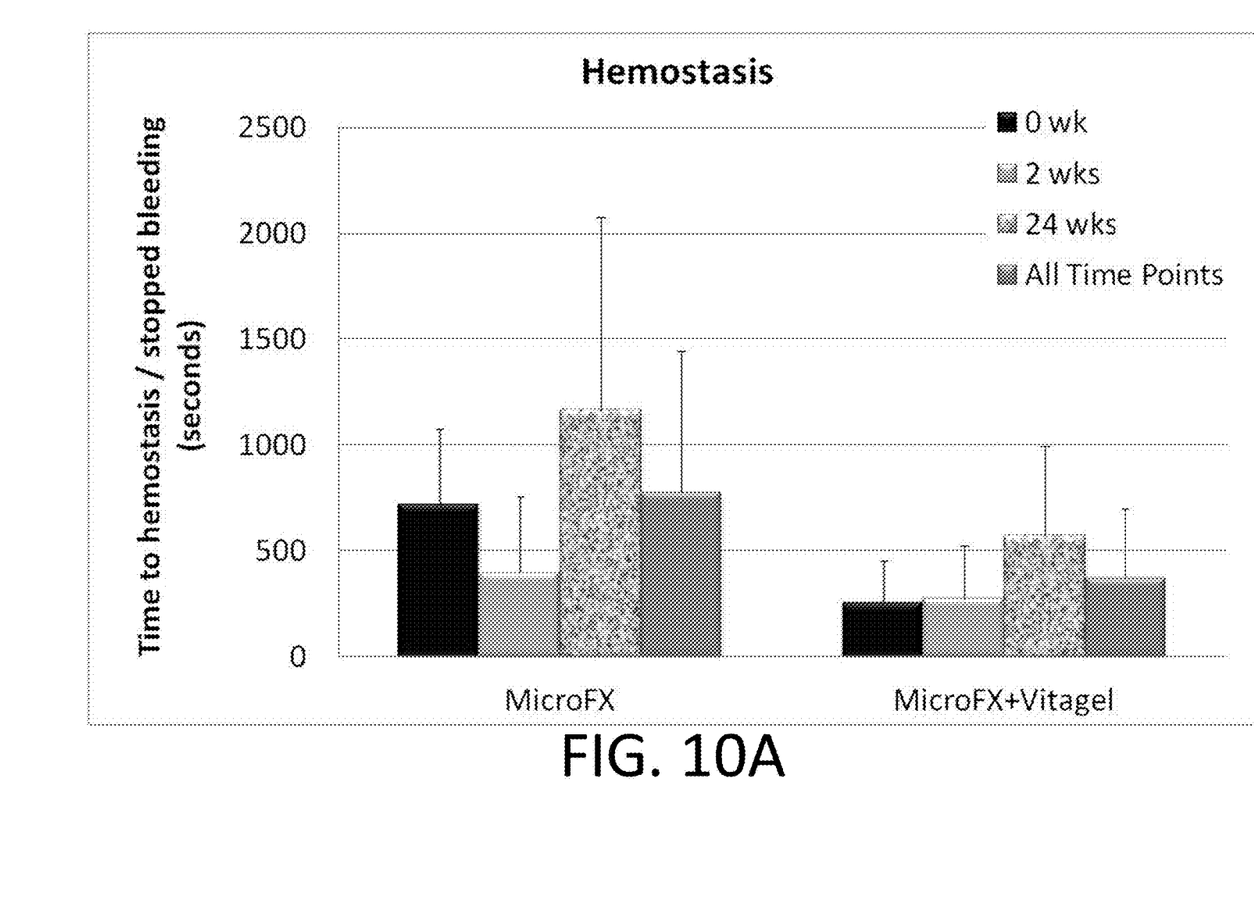
FIG. 10A is graphical representation of the in-vivo ovine study hemostasis results immediately following surgery for the animals in each group (e.g., the t=0 wk-animals, the t=2 wk-animals, and the t=24 wk-animals all immediately post-surgery; and the entire data set pooled immediately post-surgery ("All Time Points")) for the test ("MicroFX+Vitagel"—as defined below) and control ("MicroFX" w/out Vitagel—as defined below) study groups.
Figure 10B:
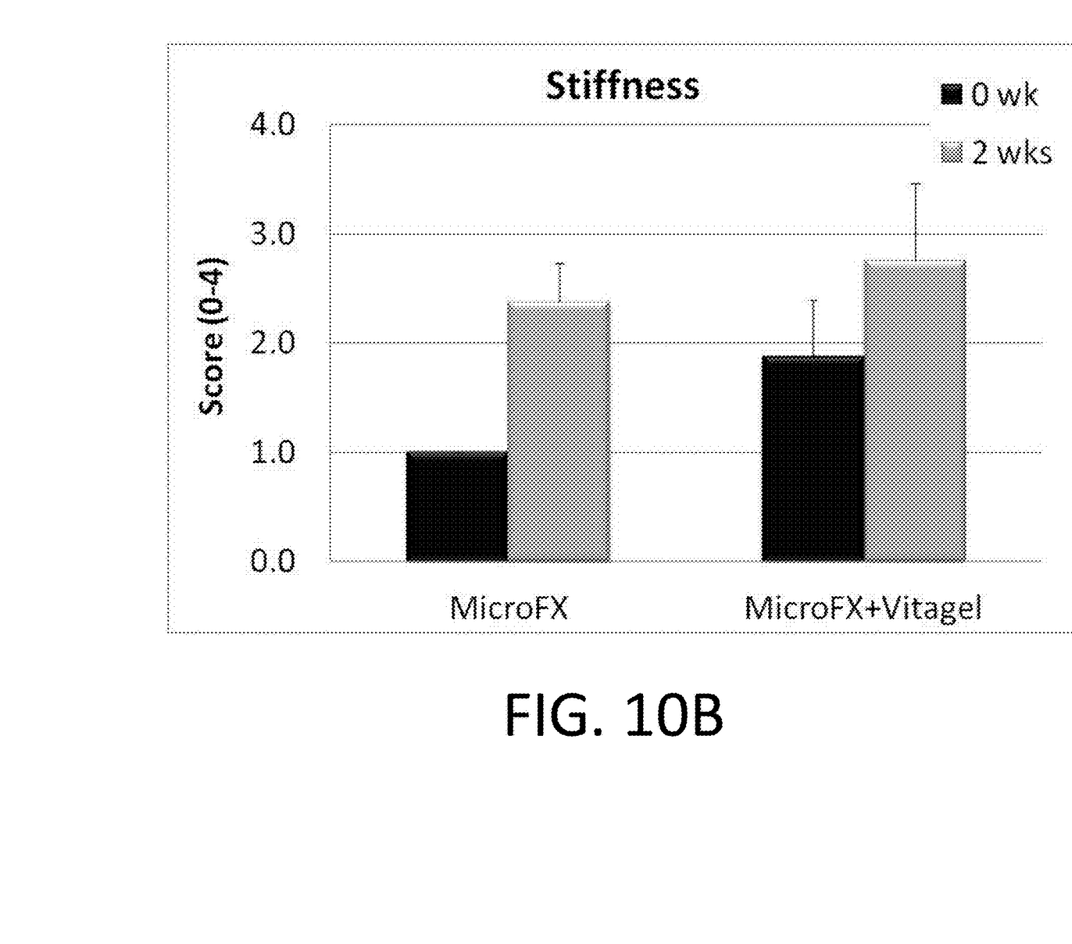
FIG. 10B is a graphical representation of the in-vivo ovine study stiffness results at t=0 wks and t=2 wks (2 weeks in vivo post-surgery) for the test ("MicroFX+Vitagel"—as defined below) and control ("MicroFX" w/out Vitagel—as defined below) study groups.

The sequence of sample preparation and analyses is illustrated in FIG. 9. Hemostasis was measured immediately after surgery for each animal in all groups (t=0, 2, and 24 weeks). Clots were formed in all sites except for two (one test and one control group in the 2 wks group. Time to hemostasis (e.g., when bleeding stopped from subchondral drilling) varied substantially between animals. However, for all animals, hemostasis was achieved faster when the present invention methodology (e.g., "MicroFX+Vitagel", is equivalent to "Vitagel+MDr") was employed in comparison to the traditional methodology (e.g., "MicroFX", is equivalent to "MDr"). Statistically, this result held true when the entire data set was pooled ("All Time Points"), as hemostasis was achieved significantly faster when the present invention test methodology ("MicroFX+Vitagel") was employed versus the control ("MicroFX" w/out Vitagel)—369 seconds vs. 776 seconds (p<0.01) (FIG. 10A). At t=0 wks, the present invention clots with Vitagel were significantly stiffer than the control blood clots (1.9 vs. 1.0, p<0.05). All clots increased in stiffness after 2 weeks in-vivo, with the present invention clots with Vitagel continuing to exhibit higher values than the control blood clots (2.8 vs. 2.4, p=0.12). (FIG. 10B)

Throughout this disclosure, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for repairing a cartilage defect comprising:
    applying a tourniquet proximal to the cartilage defect;
    preparing a cartilage defect by removing unwanted or damaged tissue;
    creating at least one perforation into or through subchondral bone, below and/or adjacent to the cartilage defect to induce the flow of bone fluid;
    allowing the bone fluid to bleed through the at least one perforation up into the cartilage defect to fill at least a portion of the cartilage defect;
    removing the tourniquet to allow uninhibited bleeding up into the cartilage defect; and
    after removing the tourniquet and allowing at least some bleeding into the cartilage defect to form a bloody bed in the cartilage defect, applying a surgical hemostat including thrombin and collagen into the bone fluid of the bloody bed so that the surgical hemostat intermixes with the bone fluid of the bloody bed to produce a clot for cartilage regeneration,
    wherein the intermixing of the surgical hemostat and the bone fluid forms an enhanced clot in the cartilage defect, and
    wherein the enhanced clot includes a matrix structure through which additional bone fluid migrates to replenish nutrients within the cartilage defect.

2. The method of claim 1, wherein the surgical hemostat is applied to the defect after bone fluid bleeds into the defect to fill at least a portion of the defect.

3. The method of claim 1, wherein the bone fluid and the applied surgical hemostat completely fill the cartilage defect.

4. The method of claim 1, wherein the bone fluid comprises blood, bone marrow, cells, or any combination.

5. The method of claim 1, wherein the step of applying the surgical hemostat results in the surgical hemostat positioned within the cartilage defect while the at least one perforation is substantially free of the surgical hemostat.

6. The method of claim 1, wherein the step of creating the at least one perforation is performed using an awl or pick.

7. The method of claim 1, wherein the collagen of the surgical hemostat is a microfibrillar collagen with fibrils between 3 nm and 30 nm in diameter and a melting temperature between 42° C. and 46° C.

8. The method of claim 1, wherein the step of creating the at least one perforation is performed using a drill.

9. The method of claim 8, wherein the drill includes a flexible drill and a curved drill guide adapted to direct the flexible drill along a predetermined angle of curvature.

10. A kit for repairing a cartilage defect comprising:
    a bone marrow stimulation instrument comprising at least one drill guide and a drill;
    a cap adapted to prevent migration of bone fluid, migrating into the cartilage defect through perforations in subchondral bone below and/or adjacent to the cartilage defect formed by the bone marrow stimulation instrument, away from the cartilage defect, the cap including a cannula and a filter positioned within the cannula, wherein the filter is adapted to extract extrudate from the bone fluid; and
    a surgical hemostat including collagen and thrombin, the surgical hemostat adapted to form an enhanced clot when applied to the bone fluid in the cartilage defect so that the surgical hemostat intermixes with the bone fluid, the enhanced clot including a matrix structure through which additional bone fluid migrates to replenish nutrients within the cartilage defect.

11. The kit of claim 10, wherein the collagen of the surgical hemostat is a microfibrillar collagen with fibrils between 3 nm and 30 nm in diameter and a melting temperature between 42° C. and 46° C.

12. The kit of claim 11, wherein the surgical hemostat further comprises polyethylene glycol in a concentration of 0.1 to 2.0%.

13. A method for creating a healing matrix for a cartilage defect in-situ comprising:
    preparing a cartilage defect by removing unwanted or damaged tissue;
    creating at least one perforation into or through subchondral bone below and/or adjacent to the cartilage defect to induce the flow of bone fluid;
    positioning a cap over the cartilage defect and at least one perforation;
    allowing the bone fluid to bleed through the at least one perforation up into the cartilage defect to fill at least a portion of the cartilage defect and form a bloody bed, the cap preventing the bone fluid from migrating out of the cartilage defect; and
    after the bone fluid at least partially bleeds through the at least one perforation up into a defect area of the cartilage defect and a bloody bed is formed, applying a biomaterial into the bone fluid of the bloody bed in the defect area so that the biomaterial intermixes with the bone fluid to produce a clot for cartilage regeneration,
    wherein the intermixing of the biomaterial and the bone fluid in the defect area forms an enhanced clot, and
    wherein the enhanced clot includes a matrix structure through which additional bone fluid migrates to replenish nutrients within the cartilage defect.

14. The method of claim 13, wherein the biomaterial is applied to the cartilage defect through a cannulation in the cap.

15. The method of claim 13, wherein the steps of the method are performed arthroscopically.

16. The method of claim 13, further comprising the step of removing the cap once the enhanced clot stabilizes.

17. The method of claim 13, wherein the biomaterial includes a surgical hemostat.

18. The method of claim 17, wherein the surgical hemostat includes thrombin and a microfibrillar collagen having fibrils between 3 nm and 30 nm in diameter and a melting temperature between 42° C. and 46° C.

19. The method of claim 13, further comprising the step of providing suction to the cartilage defect, through a cannulation in the cap, to promote bleeding of bone fluid through the at least one perforation up into the cartilage defect.

20. The method of claim 19, further comprising a filter positioned within the cannulation to allow flow of an exudate portion of the bone fluid out of the cap through the filter and cannulation but prevent the flow of cells, platelets and nutrients from exiting the cap.

* * * * *